US008008502B2

(12) United States Patent
Bergeron

(10) Patent No.: US 8,008,502 B2
(45) Date of Patent: Aug. 30, 2011

(54) THIAZOLINE ACID DERIVATIVES

(75) Inventor: Raymond J. Bergeron, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 99 days.

(21) Appl. No.: 12/383,854

(22) Filed: Mar. 27, 2009

(65) Prior Publication Data
US 2010/0094016 A1 Apr. 15, 2010

Related U.S. Application Data

(63) Continuation of application No. 11/522,299, filed on Sep. 15, 2006, now Pat. No. 7,531,563, which is a continuation of application No. 10/944,150, filed on Sep. 17, 2004, now Pat. No. 7,126,004, which is a continuation of application No. 10/300,071, filed on Nov. 20, 2002, now abandoned, which is a continuation of application No. 09/531,753, filed on Mar. 20, 2000, now Pat. No. 6,559,315, which is a continuation of application No. 09/144,103, filed on Aug. 31, 1998, now Pat. No. 6,083,966.

(51) Int. Cl.
C07D 277/08 (2006.01)

(52) U.S. Cl. .......................... 548/201; 548/146; 548/200

(58) Field of Classification Search .................. 548/146, 548/200, 201
See application file for complete search history.

(56) References Cited

U.S. PATENT DOCUMENTS

| | | | |
|---|---|---|---|
| 3,274,207 A | 9/1966 | Kollonitsch et al. | |
| 3,809,754 A | 5/1974 | Bertrand | |
| 3,882,110 A | 5/1975 | Clemence et al. | |
| 4,367,233 A | 1/1983 | Clark et al. | |
| 4,406,905 A | 9/1983 | Zahner et al. | |
| 4,457,935 A | 7/1984 | Iwao et al. | |
| 4,457,936 A | 7/1984 | Draeger et al. | |
| 4,558,059 A | 12/1985 | Kawasaki et al. | |
| 4,736,060 A | 4/1988 | Tomuro et al. | |
| 4,775,675 A | 10/1988 | Gyorgydeak et al. | |
| 4,902,700 A | 2/1990 | Hayasi et al. | |
| 4,914,208 A | 4/1990 | Jakob et al. | |
| 5,084,083 A | 1/1992 | Lewis et al. | |
| 5,106,992 A | 4/1992 | Magnin et al. | |
| 5,169,858 A | 12/1992 | Rubin | |
| 5,182,402 A | 1/1993 | Lewis et al. | |
| 5,192,781 A | 3/1993 | Bru-Magniez et al. | |
| 5,385,922 A | 1/1995 | Bron et al. | |
| 5,393,777 A | 2/1995 | Crosa | |
| 5,442,073 A | 8/1995 | Eicken et al. | |
| 5,614,520 A | 3/1997 | Kondo et al. | |
| 5,840,739 A | 11/1998 | Bergeron, Jr. | |
| 6,080,764 A | 6/2000 | Chihiro et al. | |
| 6,083,966 A | 7/2000 | Bergeron, Jr. | |
| 6,147,070 A | 11/2000 | Facchini | |
| 6,159,983 A | 12/2000 | Bergeron, Jr. | |
| 6,251,927 B1 | 6/2001 | Lai et al. | |
| 6,373,912 B1 | 4/2002 | Yu | |
| 6,437,143 B2 | 8/2002 | Moinet et al. | |
| 6,521,652 B1 | 2/2003 | Bergeron | |
| 6,525,080 B1 | 2/2003 | Bergeron | |
| 6,559,315 B1 | 5/2003 | Bergeron | |
| 6,864,270 B2 | 3/2005 | Bergeron, Jr. | |
| RE39,132 E * | 6/2006 | Bergeron, Jr. | 514/365 |
| 7,126,004 B2 | 10/2006 | Bergeron | |
| 7,144,904 B2 | 12/2006 | Bergeron, Jr. | |
| 7,531,563 B2 | 5/2009 | Bergeron | |
| 2002/0049316 A1 | 4/2002 | Halbert et al. | |
| 2003/0236417 A1 | 12/2003 | Bergeron | |
| 2004/0044220 A1 | 3/2004 | Bergeron | |
| 2004/0132789 A1 | 7/2004 | Bergeron | |
| 2005/0033057 A1 | 2/2005 | Bergeron | |
| 2005/0234113 A1 | 10/2005 | Bergeron | |
| 2006/0211746 A1 | 9/2006 | Bergeron | |
| 2007/0238767 A1 | 10/2007 | Bergeron | |
| 2008/0214630 A1 | 9/2008 | Bergeron | |
| 2010/0093812 A1 | 4/2010 | Bergeron, Jr. | |
| 2010/0137346 A1 | 6/2010 | Bergeron, Jr. | |

FOREIGN PATENT DOCUMENTS

| | | |
|---|---|---|
| CS | 205217 B1 | 5/1981 |
| DE | 2245560 A1 | 3/1974 |
| DE | 3002989 A1 | 7/1981 |
| EP | 0 214 101 A2 | 3/1987 |
| EP | 0 214 933 A2 | 3/1987 |
| EP | 0 325 559 A2 | 7/1989 |
| EP | 0 513 379 A1 | 11/1992 |
| GB | 1292170 A | 10/1972 |
| GB | 1320534 A | 6/1973 |
| GB | 1382887 A | 2/1975 |
| JP | 57-058682 A | 4/1982 |
| WO | WO-94/11367 A1 | 5/1994 |
| WO | WO-97/36885 A1 | 10/1997 |
| WO | WO-99/53039 A1 | 10/1999 |

(Continued)

OTHER PUBLICATIONS

European Supplementary Search Report for EP 07874513.0 mailed Jan. 19, 2010.
International Search Report and Written Opinion for PCT/US2007/025377 mailed Jan. 8, 2009.
International Preliminary Report on Patentability for PCT/US2007/025377 mailed Jun. 23, 2009.
International Search Report and Written Opinion for PCT/US2008/003433 mailed Jun. 19, 2008.
International Preliminary Report on Patentability for PCT/US2008/003433 mailed Sep. 24, 2009.
International Search Report and Written Opinion for PCT/US2003/028304 mailed Mar. 5, 2004.

(Continued)

Primary Examiner — Golam M Shameem
(74) Attorney, Agent, or Firm — Wolf, Greenfield & Sacks, P.C.; Edward R. Gates; C. Hunter Baker

(57) ABSTRACT

The present invention relates to novel thiazoline acids and derivatives thereof useful as chelators of trivalent metals in therapeutic applications. For example, the thiazoline acid derivatives are useful in diagnosing and treating pathological conditions associated with an excess of trivalent metals in humans and animals.

18 Claims, 1 Drawing Sheet

FOREIGN PATENT DOCUMENTS

| WO | WO-00/12493 A1 | 3/2000 |
|---|---|---|
| WO | WO-00/16763 A2 | 3/2000 |
| WO | WO-01/27119 A2 | 4/2001 |
| WO | WO-2004/017959 A2 | 3/2004 |
| WO | WO-2005/023310 A2 | 3/2005 |
| WO | WO-2005/034949 A1 | 4/2005 |
| WO | WO-2006/055412 A1 | 5/2006 |
| WO | WO-2006/107626 A1 | 10/2006 |

OTHER PUBLICATIONS

International Search Report and Written Opinion for PCT/US2006/010945 mailed Aug. 9, 2006.
International Preliminary Report on Patentability for PCT/US2006/010945 mailed Oct. 18, 2007.
European Supplementary Search Report for EP 99945267.5 mailed Dec. 5, 2001.
International Search Report for PCT/US1999/019691 mailed Jan. 19, 2000.
Written Opinion for PCT/US1999/019691 mailed Aug. 21, 2000.
International Preliminary Examination Report for PCT/US1999/019691 mailed Feb. 2, 2001.
Office Communication for U.S. Appl. No. 11/367,042 mailed Jun. 12, 2008.
Office Communication for U.S. Appl. No. 11/367,042 mailed Feb. 27, 2009.
Office Communication for U.S. Appl. No. 11/367,042 mailed Nov. 2, 2009.
Office Communication for U.S. Appl. No. 11/367,042 mailed Jun. 10, 2010.
Office Communication for U.S. Appl. No. 11/973,001 mailed Sep. 23, 2010.
Office Communication for U.S. Appl. No. 09/144,103 mailed Sep. 30, 1998.
Office Communication for U.S. Appl. No. 09/144,103 mailed Feb. 11, 1999.
Notice of Allowance for U.S. Appl. No. 09/144,103 mailed Oct. 21, 1999.
Office Communication for U.S. Appl. No. 09/981,586 mailed Jan. 31, 2003.
Office Communication for U.S. Appl. No. 09/981,586 mailed Jun. 16, 2003.
Office Communication for U.S. Appl. No. 09/981,586 mailed Feb. 24, 2004.
Notice of Allowance for U.S. Appl. No. 09/981,586 mailed Jan. 27, 2005.
Office Communication for U.S. Appl. No. 09/531,753 mailed Nov. 3, 2000.
Office Communication for U.S. Appl. No. 09/531,753 mailed Jun. 11, 2001.
Notice of Allowance for U.S. Appl. No. 09/531,753 mailed Aug. 27, 2002.
Office Communication for U.S. Appl. No. 09/531,754 mailed Nov. 13, 2000.
Office Communication for U.S. Appl. No. 09/531,754 mailed Jun. 11, 2001.
Notice of Allowance for U.S. Appl. No. 09/531,754 mailed Aug. 27, 2002.
Office Communication for U.S. Appl. No. 09/531,755 mailed Nov. 3, 2000.
Office Communication for U.S. Appl. No. 09/531,755 mailed Jun. 11, 2001.
Notice of Allowance for U.S. Appl. No. 09/531,755 mailed Aug. 27, 2002.
Office Communication for U.S. Appl. No. 10/300,071 mailed Oct. 22, 2004.
Office Communication for U.S. Appl. No. 10/944,150 mailed Oct. 12, 2005.
Notice of Allowance for U.S. Appl. No. 10/944,150 mailed Jun. 29, 2006.
Office Communication for U.S. Appl. No. 11/522,299 mailed Jul. 17, 2008.
Notice of Allowance for U.S. Appl. No. 11/522,299 mailed Dec. 31, 2008.
[No Author Listed] Database CHEMCATS, Accession No. 2003:2524667; TimTec Overseas Stock; May 19, 2003.
[No Author Listed] Highlights of Prescribing Information: EXJADE. Novartis Pharma Stein AG. 2010. Available at http://www.pharma.us.novartis.com/product/pi/pdf/exjade.pdf. Last accessed Sep. 9, 2010. 14 pages.
[No Author Listed] "Ion exchanger." Ullmanns Encyclopedia of Industrial Chemistry. 5th Ed. vol. 14A:446-56.
Anderegg et al., Metal Complex Formation of a New Siderophore Desferrithiocin and of Three Related Ligands. J Chem Soc Chem Commun. 1990:1194-96.
Angelucci et al., Hepatic iron concentration and total body iron stores in thalassemia major. N Engl J Med. Aug. 3, 2000;343(5):327-31.
Babbs et al., Oxygen radicals in ulcerative colitis. Free Radic Biol Med. 1992;13(2):169-81.
Bergeron et al., A comparative evaluation of iron clearance models. Ann N Y Acad Sci. 1990;612:378-93.
Bergeron et al., A comparative study of the iron-clearing properties of desferrithiocin analogues with desferrioxamine B in a Cebus monkey model. Blood. Apr. 15, 1993;81(8):2166-73.
Bergeron et al., A comparison of the iron-clearing properties of 1,2-dimethyl-3-hydroxypyrid-4-one, 1,2-diethyl-3-hydroxypyrid-4-one, and deferoxamine. Blood. Apr. 1, 1992;79(7):1882-90.
Bergeron et al., An investigation of desferrithiocin metabolism. J Med Chem. Sep. 2, 1994;37(18):2889-95.
Bergeron et al., Comparison of iron chelator efficacy in iron-overloaded beagle dogs and monkeys (*Cebus apella*). Comp Med. Dec. 2004;54(6):664-72.
Bergeron et al., Desazadesmethyldesferrithiocin Analogues as Orally Effective Iron Chelators. J Med Chem. 1999;42:95-108.
Bergeron et al., Desferrithiocin analogue based hexacoordinate iron(III) chelators. J Med Chem. Jan. 2, 2003;46(1):16-24.
Bergeron et al., Effects of C-4 stereochemistry and C-4' hydroxylation on the iron clearing efficiency and toxicity of desferrithiocin analogues. J Med Chem. Jul. 1, 1999;42(13):2432-40.
Bergeron et al., Evaluation of desferrithiocin and its synthetic analogues as orally effective iron chelators. J Med Chem. Jul. 1991;34(7):2072-8.
Bergeron et al., Evaluation of the desferrithiocin pharmacophore as a vector for hydroxamates. J Med Chem. Jul. 29, 1999;42(15):2881-6.
Bergeron et al., HBED: A Potential Alternative to Deferoxamine for Iron-Chelating Therapy. Blood. 1998;91:1446-52.
Bergeron et al., Impact of the 3,6,9-Trioxadecyloxy Group on Desazadesferrithiocin Analogue Iron Clearance and Organ Distribution. J Med Chem. Jul. 12, 2007;50(14):3302-13. Epub Jun. 12, 2007.
Bergeron et al., Impact of the Lipophilicity of Desferrithiocin Analogues on Iron Clearance. Medicinal Inorg Chem. 2005:366-83.
Bergeron et al., Influence of iron on in vivo proliferation and lethality of L1210 cells. J Nutr. Mar. 1985;115(3):369-74.
Bergeron, Iron: A Controlling Nutrient in Proliferative Processes. Trends in Biochem Sci. 1986;11:133-36.
Bergeron et al., Iron chelation promoted by desazadesferrithiocin analogs: An enantioselective barrier. Chirality. Aug. 2003;15(7):593-9.
Bergeron et al., Iron Chelators and Therapeutic Uses. In: Burger's Medicinal Chemistry. 6th ed. 2003:479-561.
Bergeron et al., Metabolism and pharmacokinetics of N1,N14-diethylhomospermine. Drug Metab Dispos. Mar. 1996;24(3):334-43.
Bergeron et al., Methoxylation of desazadesferrithiocin analogues: enhanced iron clearing efficiency. J Med Chem. Apr. 10, 2003;46(8):1470-7.
Bergeron et al., Partition-variant desferrithiocin analogues: organ targeting and increased iron clearance. J Med Chem. Feb. 10, 2005;48(3):821-31.
Bergeron et al., Pharmacokinetics of orally administered desferrithiocin analogs in cebus apella primates. Drug Metab Dispos. Dec. 1999;27(12):1496-8.
Bergeron et al., (S)-4,5-dihydro-2-(2-hydroxy-4-hydroxyphenyl)-4-methyl-4-thiazolecarboxylic acid polyethers: a solution to nephrotoxicity. J Med Chem. May 4, 2006;49(9):2772-83.

Bergeron et al., Structure-activity relationships among desazadesferrithiocin analogues. In: Iron Chelation Therapy. Hershko, ed. 2002:167-84.

Bergeron et al., Synthesis and biological evaluation of hydroxamate-based iron chelators. J Med Chem. Nov. 1991;34(11):3182-7.

Bergeron et al., Synthesis and biological evaluation of naphthyldesferrithiocin iron chelators. J Med Chem. Apr. 12, 1996;39(8):1575-81.

Bergeron et al., The desferrithiocin pharmacophore. J Med Chem. May 13, 1994;37(10):1411-7.

Bergeron et al., The design, synthesis, and evaluation of organ-specific iron chelators. J Med Chem. Nov. 30, 2006;49(24):7032-43.

Bergeron et al., The origin of the differences in (R)- and (S)-desmethyldesferrithiocin. Iron-clearing properties. Ann N Y Acad Sci. Jun. 30, 1998;850:202-16.

Bickel et al., [Metabolic Properties of Actinomycetes.] Ferrioxamine B. Helv Chim Acta. 1960;43:2129-38. German.

Bierer et al., The effect of desferrithiocin, an oral iron chelator, on T-cell function. Blood. Nov. 15, 1990;76(10):2052-9.

Bonkovsky et al., Iron-induced liver injury. Clin Liver Dis. May 2000;4(2):409-29, vi-vii.

Brittenham, Disorders of Iron Metabolism: Iron Deficiency and Overload. In: Hermatology: Basic Principles and Practice. 3d Ed. Hoffman et al., eds., Churchill Livingston. New York. 2000:397-428.

Brittenham et al., Efficacy of deferoxamine in preventing complications of iron overload in patients with thalassemia major. N Engl J Med. Sep. 1, 1994;331(9):567-73.

Brittenham, Iron chelators and iron toxicity. Alcohol. Jun. 2003;30(2):151-8.

Brittenham, Pyridoxal isonicotinoyl hydrazone: an effective iron-chelator after oral administration. Semin Hematol. Apr. 1990;27(2):112-6.

Byers et al., Microbial iron transport: iron acquisition by pathogenic microorganisms. Met Ions Biol Syst. 1998;35:37-66.

Cappellini, Iron-chelating therapy with the new oral agent ICL670 (Exjade). Best Pract Res Clin Haematol. Jun. 2005;18(2):289-98.

Cario et al., Insulin sensitivity and beta-cell secretion in thalassaemia major with secondary haemochromatosis: assessment by oral glucose tolerance test. Eur J Pediatr. Mar. 2003;162(3):139-46. Epub Jan. 15, 2003.

Conrad et al., Iron absorption and transport. Am J Med Sci. Oct. 1999;318(4):213-29.

Cragg et al., The iron chelator L1 potentiates oxidative DNA damage in iron-loaded liver cells. Blood. Jul. 15, 1998;92(2):632-8.

Dean et al., The Action of Nine Chelators on Iron-Dependent Radical Damage. Free Rad Res. 1994;20(2):83-101.

Domingo et al., Comparative effects of the chelators sodium 4,5-dihydroxybenzene-1,3-disulfonate (Tiron) and diethylenetriaminepentaacetic acid (DTPA) on acute uranium nephrotoxicity in rats. Toxicology. Mar. 14, 1997;118(1):49-59.

Donovan et al., Preclinical and clinical development of deferitrin, a novel, orally available iron chelator. Ann N Y Acad Sci. 2005;1054:492-4.

Durbin et al., Chelating agents for uranium(VI): 2. Efficacy and toxicity of tetradentate catecholate and hydroxypyridinonate ligands in mice. Health Phys. May 2000;78(5):511-21.

Durbin et al., In Vivo Chelation of Am(III), Pu(IV), Np(V), and U(VI) in Mice by TREN-(Me-3,2-HOPO). Radiat Prot Dosimetry. 1994;53:305-09.

Farcasiu et al., Geometrical inversion of methoxymethyl cations. J Chem Soc Chem Commun. 1979;24:1124-5.

Finch et al., Ferrokinetics in man. Medicine (Baltimore). Jan. 1970;49(1)17-53.

Finch et al., Perspectives in iron metabolism. N Engl J Med. Jun. 24, 1982;306(25):1520-8.

Fossheim et al., Lanthanide-based susceptibility contrast agents: assessment of the magnetic properties. Magn Reson Med. Feb. 1996;35(2):201-6.

Fritsch et al., Plasmodium falciparum: inhibition in vitro with lactoferrin, desferriferrithiocin, and desferricrocin. Exp Parasitol. Feb. 1987;63(1):1-9.

Fukuda, Chelating agents used for plutonium and uranium removal in radiation emergency medicine. Curr Med Chem. 2005;12(23):2765-70.

Galanello et al., Safety, tolerability, and pharmacokinetics of ICL670, a new orally active iron-chelating agent in patients with transfusion-dependent iron overload due to beta-thalassemia. J Clin Pharmacol. Jun. 2003;43(6):565-72.

Ganguly et al., Antiviral activity of isoquinolines carbazoles and other miscellaneous synthetic chemicals in mice. Indian J Med Res. Oct. 1975;63(10):1418-25.

Giardina et al., Chelation therapy in beta-thalassemia: an optimistic update. Semin Hematol. Oct. 2001;38(4):360-6.

Golub et al., Molecular classification of cancer: class discovery and class prediction by gene expression monitoring. Science. Oct. 15, 1999;286(5439):531-7.

Gorden et al., Rational design of sequestering agents for plutonium and other actinides. Chem Rev. Nov. 2003;103(11):4207-82.

Grady et al., HBED: a potential oral iron chelator. Ann N Y Acad Sci. 1990;612:361-8.

Grady et al., Rhodotorulic acid—investigation of its potential as an iron-chelating drug. J Pharmacol Exp Ther. Jun. 1979;209(3):342-8.

Graf et al., Iron-catalyzed hydroxyl radical formation. Stringent requirement for free iron coordination site. J Biol Chem. Mar. 25, 1984;259(6):3620-4.

Guilmette et al., Competitive binding of Pu and Am with bone mineral and novel chelating agents. Radiat Prot Dosimetry. 2003;105(1-4):527-34.

Guterman et al., Feasibility of enterochelin as an iron-chelating drug: studies with human serum and a mouse model system. Gen Pharmacol. 1978;9(2):123-7.

Hahn et al., Coordination Chemistry of Microbial Iron Transport. 42. Structural and Spectroscopic Characterization of Diastereomeric Cr(III) and Co(III) Complexes of Desferriferrithiocin. J Am Chem Soc. 1990;112:1854-60.

Hallberg, Bioavailability of dietary iron in man. Ann Rev Nutr. 1981;1:123-47.

Halliwell, Free radicals and antioxidants: a personal view. Nutr Rev. Aug. 1994;52(8 Pt 1):253-65.

Halliwell, Iron, Oxidative Damage and Chelating Agents. In: The Development of Iron Chelators for Clinical Use, Bergeron, ed. 1994:33-56.

Hazen et al., Human neutrophils employ the myeloperoxidase-hydrogen peroxide-chloride system to oxidize alpha-amino acids to a family of reactive aldehydes. Mechanistic studies identifying labile intermediates along the reaction pathway. J Biol Chem. Feb. 27, 1998;273(9):4997-5005.

Henry, Chemotherapeutic nitroheterocycles. Derivatives of 5-nitrothiazole-2-carboxaldehyde and 5-nitrothiazole-2-carboxylic acid. J Med Chem. Mar. 1969;12(2):303-6.

Hoffbrand et al., Long-term trial of deferiprone in 51 transfusion-dependent iron overloaded patients. Blood. Jan. 1, 1998;91(1):295-300.

Hoffbrand, Transfusion Siderosis and Chelation Therapy. Iron in Biochemistry and Medicine. vol. II. London. 1980: 449-527.

Jalal et al., Structure of Anguibactin, a Unique Plasmid-Related Bacterial Siderophore from the Fish Pathogen Vibrio Anguillarum. J Am Chem Soc. 1989;111(1):292-96.

Jarvis et al., Some correlations involving the stability of complexes of transuranium metal ions and ligands with negatively charged oxygen donors. Inorg Chim Acta. 1991;182:229-32.

Kalinowski et al., The evolution of iron chelators for the treatment of iron overload disease and cancer. Pharmacol Rev. Dec. 2005;57(4):547-83.

Kersten et al., Long-term treatment of transfusional iron overload with the oral iron chelator deferiprone (L1): a Dutch multicenter trial. Ann Hematol. Nov. 1996;73(5):247-52.

Kicic et al., The desferrithiocin (DFT) class of iron chelators: potential as antineoplastic agents. Anticancer Drug Des. Aug.-Oct. 2001;16(4-5):195-207.

Kishore et al., Synthesis of α-Poly-[Nε-2-aryl-Δ2-thiazoline-4-carbonyl-L-lysine] with Antival Activity. Ind J Chem. 1977;15B:255-57.

Kontoghiorghes et al., 1,2-Dimethyl-3-hydroxypyrid-4-one, an orally active chelator for treatment of iron overload. Lancet. Jun. 6, 1987;1(8545):1294-5.

Koppenol, Kinetics and Mechanisms of the Fenton Reaction: Implications in Iron Toxicity. In: Iron Chelators: New Development Strategies, Bergeron, ed., 2000:3-10.

Langer et al., Solid complexes with tetravalent metal ions and ethylenediamime tetra-acetic acid (EDTA). J Inorg Nucl Chem. 1964;26:59-72.

Lieu et al., The roles of iron in health and disease. Mol Aspects Med. Feb.-Apr. 2001;22(1-2):1-87.

Luciani et al., Americium in the beagle dog: biokinetic and dosimetric model. Health Phys. May 2006;90(5):459-70.

Miller et al., Efficacy of orally administered amphipathic polyaminocarboxylic acid chelators for the removal of plutonium and americium: comparison with injected Zn-DTPA in the rat. Radiat Prot Dosimetry. 2006;118(4):412-20. Epub Dec. 6, 2005.

Naegeli et al., [Metabolites of Microorganisms.] Part 193. Ferrithiocin. Hely Chim Acta. 1980;63:1400-06. German.

Nash et al., Features of the thermodynamics of two-phase distribution reactions of americium(III) and europium(III) nitrates into solutions of 2,6-bis[(bis(2-ethylhexyl)phosphino)methyl]pyridine N,P,P'-trioxide. Inorg Chem. Nov. 4, 2002;41(22):5849-58.

Neu et al., Structural Characterization of a Plutonium(IV) Siderophore Complex: Single-Crystal Structure of Pu-Desferrioxamine E. Angew Chem Int Ed Engl. Apr. 2000;39(8):1442-1444.

Nisbet-Brown et al., Effectiveness and safety of ICL670 in iron-loaded patients with thalassaemia: a randomised, double-blind, placebo-controlled, dose-escalation trial. Lancet. May 10, 2003;361(9369):1597-602.

O'Connell et al., The role of iron in ferritin- and haemosiderin-mediated lipid peroxidation in liposomes. Biochem J. Jul. 1, 1985;229(1):135-9.

Olivieri et al., Iron-chelating therapy and the treatment of thalassemia. Blood. Feb. 1, 1997;89(3):739-61.

Olivieri et al., Long-term safety and effectiveness of iron-chelation therapy with deferiprone for thalassemia major. N Engl J Med. Aug. 13, 1998;339(7):417-23.

Olivieri, Long-term therapy with deferiprone. Acta Haematol. 1996;95(1):37-48.

Østergaard et al., Evalution of capillary electrophoresis-frontal analysis for the study of low molecular weight drug-human serum albumin interactions. Electrophoresis. Sep. 2002;23(17):2842-53.

Paquet et al., Efficacy of 3,4,3-LI(1,2-HOPO) for decorporation of Pu, Am and U from rats injected intramuscularly with high-fired particles of MOX. Radiat Prot Dosimetry. 2003;105(1-4):521-5.

Pashalidis et al., Effective complex formation in the interaction of 1,2-dimethyl-3-hydroxypyrid-4-one (Deferiprone or L1) with uranium (VI). J Radioanal Nucl Chem. 1999;242:181-84.

Pietrangelo, Mechanism of iron toxicity. In: Iron Chelation Therapy. Hershko, ed. 2002:19-43.

Pippard et al., Iron chelation using subcutaneous infusions of diethylene triamine penta-acetic acid (DTPA). Scand J Haematol. May 1986;36(5):466-72.

Pippard, Desferrioxamine-induced iron excretion in humans. Baillieres Clin Haematol. Apr. 1989;2(2):323-43.

Ponka et al., Function and regulation of transferrin and ferritin. Semin Hematol. Jan. 1998;35(1):35-54.

Ponka et al., Mobilization of iron from reticulocytes. Identification of pyridoxal isonicotinoyl hydrazone as a new iron chelating agent. FEBS Lett. Jan. 15, 1979;97(2):317-21.

Rao et al., Complexation of Thorium(IV) with Desmethyldesferrithiocin. Radiochim Acta. 2000;88:851-56.

Raymond et al., Coordination Chemistry and Microbial Iron Transport. Acc Chem Res. 1979;12:183-190.

Re et al., Antioxidant activity applying an improved ABTS radical cation decolorization assay. Free Radic Biol Med. May 1999;26(9-10):1231-7.

Richardson, The controversial role of deferiprone in the treatment of thalassemia. J Lab Clin Med. May 2001;137(5):324-9.

Santos et al., A cyclohexane-1, 2-diyldinitrilotetraacetate tetrahydroxamate derivative for actinide complexation: Synthesis and complexation studies. J Chem Soc Dalton Trans. 2000:4398-4402.

Seligman et al., Molecular Mechanisms of Iron Metabolism. The Molecular Basis of Blood Diseases. 1987;219-44.

Souillac et al., "Characterization of Deliver Systems, Differential Scanning in Calorimetry." Encyclopedia of Controlled Drug Delivery. John Wiley & Sons. 1999:212-27.

Stahel et al., Iron chelators: in vitro inhibitory effect on the liver stage of rodent and human malaria. Am J Trop Med Hyg. Sep. 1988;39(3):236-40.

Stradling et al., Recent developments in the decorpoartion of plutonium, americium and thorium. Radiat Prot Dosimetry. 1998;79:445-48.

Supkowski et al., Displacement of Inner-Sphere Water Molecules from Eu(3+) Analogues of Gd(3+) MRI Contrast Agents by Carbonate and Phosphate Anions: Dissociation Constants from Luminescence Data in the Rapid-Exchange Limit. Inorg Chem. Nov. 29, 1999;38(24):5616-5619.

Taetle et al., Combination iron depletion therapy. J Natl Cancer Inst. Aug. 16, 1989;81(16):1229-35.

Tang et al., High-resolution magnetic resonance imaging tracks changes in organ and tissue mass in obese and aging rats. Am J Physiol Regul Integr Comp Physiol. Mar. 2002;282(3): R890-9.

Theil et al., Ferritin Mineralization: Ferroxidation and Beyond. J Inorg Biochem. 1997;67:30. Abstract B13.

Thomas et al., Ferritin and superoxide-dependent lipid peroxidation. J Biol Chem. Mar. 25, 1985;260(6):3275-80.

Trokowski et al., Cyclen-based phenylboronate ligands and their Eu3+ complexes for sensing glucose by MRI. Bioconjug Chem. Nov.-Dec. 2004;15(6):1431-40.

Uhlir et al., Specific sequestering agents for the actinides. 21. Synthesis and initial biological testing of octadentate mixed catecholate-hydroxypyridinonate ligands. J Med Chem. Feb. 19, 1993;36(4):504-9.

Vichinsky, Current issues with blood transfusions in sickle cell disease. Semin Hematol. Jan. 2001;38(1 Suppl 1):14-22.

Vippagunta et al., Crystalline solids. Adv Drug Deliv Rev. May 16, 2001;48(1):3-26.

Weintraub et al., The treatment of hemochromatosis by phlebotomy. Med Clin North Am. Nov. 1966;50(6):1579-90.

Whisenhunt et al., Specific Sequestering Agents for the Actinides. 29. Stability of the Thorium(IV) Complexes of Desferrioxamine B (DFO) and Three Octadentate Catecholate or Hydroxypyridinonate DFO Derivatives: DFOMTA, DFOCAMC, and DFO-1,2-HOPO. Comparative Stability of the Plutonium(IV) DFOMTA Complex(1). Inorg Chem. Jul. 3, 1996;35(14):4128-4136.

Woessner et al., Numerical solution of the Bloch equations provides insights into the optimum design of PARACEST agents for MRI. Magn Reson Med. Apr. 2005;53(4):790-9.

Wojcik et al., Natural history of C282Y homozygotes for hemochromatosis. Can J Gastroenterol. May 2002;16(5):297-302.

Wolfe et al., A non-human primate model for the study of oral iron chelators. Br J Haematol. Jul. 1989;72(3):456-61.

Wood et al., The metabolism of iron-dextran given as a total-dose infusion to iron deficient Jamaican subjects. Br J Haematol. Feb. 1968:14(2):119-29.

Zacharski et al., Reduction of iron stores and cardiovascular outcomes in patients with peripheral arterial disease: a randomized controlled trial. JAMA. Feb. 14, 2007;297(6):603-10.

Zhang et al., A novel europium(III)-based MRI contrast agent. J Am Chem Soc. Feb. 21, 2001;123(7):1517-8.

Zhang et al., A paramagnetic CEST agent for imaging glucose by MRI. J Am Chem Soc. Dec. 17, 2003;125(50):15288-9.

Zurlo et al., Survival and causes of death in thalassaemia major. Lancet. Jul. 1, 1989;2(8653):27-30.

* cited by examiner

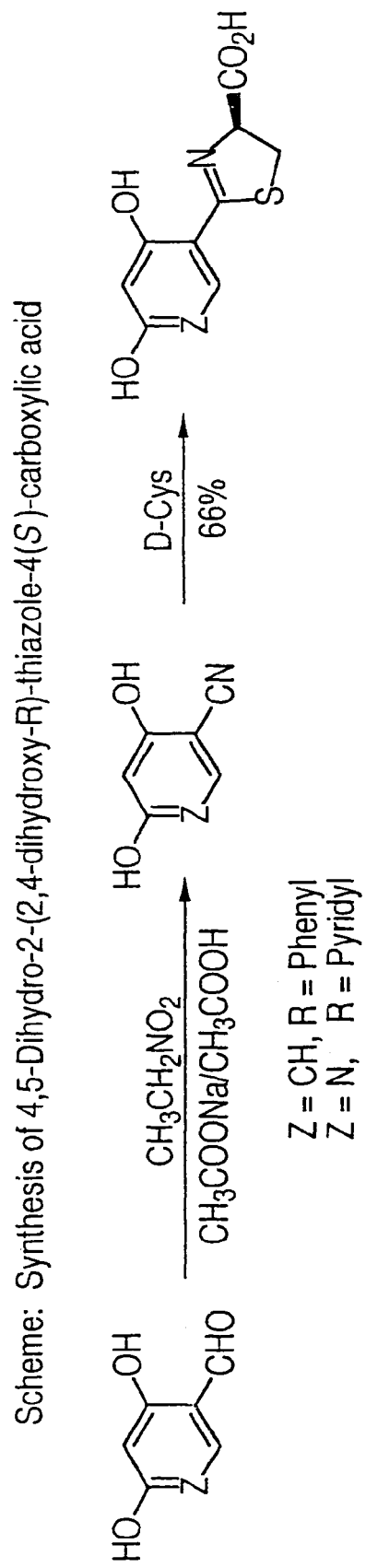
Scheme: Synthesis of 4,5-Dihydro-2-(2,4-dihydroxy-R)-thiazole-4(S)-carboxylic acid

THIAZOLINE ACID DERIVATIVES

RELATED APPLICATIONS

This application is a continuation of U.S. application Ser. No. 11/522,299, filed Sep. 15, 2006 now U.S. Pat. No. 7,531,563, which is a continuation of U.S. application Ser. No. 10/944,150, filed Sep. 17, 2004 now U.S. Pat. No. 7,126,004, which is a continuation of U.S. application Ser. No. 10/300,071, filed Nov. 20, 2002 now abandoned, which is a continuation of U.S. application Ser. No. 09/531,753, filed Mar. 20, 2000, and issued on May 6, 2003, as U.S. Pat. No. 6,559,315, which is a continuation of U.S. application Ser. No. 09/144,103, filed Aug. 31, 1998, and issued on Jul. 4, 2000 as U.S. Pat. No. 6,083,966 and reissued as RE39,132. The entire teachings of the above applications are incorporated herein by reference.

GOVERNMENT SUPPORT

Research leading to the completion of the invention was supported in part by Grant Nos. 3203522-12, RO1HL42817 and RO1DK49108 awarded by the National Institutes of Health (NIH). The United States Government has certain rights in and to the claimed invention.

BACKGROUND OF THE INVENTION

While many organisms are auxotrophic for Fe(III), because of the insolubility of the hydroxide ($K_{sp}=1\times10^{-38}$) [Acc. Chem. Res., Vol. 12, Raymond et al., "Coordination Chemistry and Microbial Iron Transport," pages 183-190 (1979)] formed under physiological conditions, nature has developed rather sophisticated iron storage and transport systems. Micro-organisms utilize low molecular weight ligands, siderophores, while eukaryotes tend to utilize proteins to transport iron, e.g. transferrin, and store iron, e.g., ferritin [Trends in Biochem. Sci., Vol. 11, Bergeron, "Iron: A Controlling Nutrient in Proliferative Processes," pages 133-136 (1986)].

Iron metabolism in primates is characterized by a highly efficient recycling process with no specific mechanism for eliminating this transition metal [Clin. Biochem., Vol. 4, Finch et al, "Iron Metabolism," pages 5-10 (1986); Ann. Rev. Nutri., Vol. 1, Hallberg, "Bioavailability of Dietary Iron in Man," pages 123-147 (1981); N. Engl. J. Med., Vol. 306, Finch et al, "Perspectives in Iron Metabolism," pages 1520-1528 (1982); and Medicine (Baltimore), Vol. 49, Finch et al, "Ferrokinetics in Man," pages 17-53 (1970)]. Because it cannot be effectively cleared, the introduction of "excess iron" into this closed metabolic loop leads to chronic overload and ultimately to peroxidative tissue damage [The Molecular Basis of Blood Diseases, Seligman et al, "Molecular Mechanisms of Iron Metabolism," page 219 (1987); Biochem. J., Vol. 229, O'Connell et al, "The Role of Iron in Ferritin- and Haemosiderin-Mediated Lipid Peroxidation in Liposomes," pages 135-139 (1985); and J. Biol. Chem., Vol. 260, Thomas et al, "Ferritin and Superoxide-Dependent Lipid Peroxidation," pages 3275-3280 (1985)]. There are a number of scenarios which can account for "iron overload," e.g., high-iron diet, acute iron ingestion or malabsorption of the metal: In each of these situations, the patient can be treated by phlebotomy [Med. Clin. N. Am., Vol. 50, Weintraub et al, "The Treatment of Hemochromatosis by Phlebotomy," pages 1579-1590 (1966)]. However, there are iron-overload syndromes secondary to chronic transfusion therapy, e.g., aplastic anemia and thalassemia, in which phlebotomy is not an option [Iron in Biochemistry and Medicine, Vol. II, Hoffbrand, "Transfusion Siderosis and Chelation Therapy," page 499 (London, 1980)]. The patient cannot be bled, as the origin of the excess iron is the transfused red blood cells; thus, the only alternative is chelation therapy. However, to be therapeutically effective, a chelator must be able to remove a minimum of between 0.25 and 0.40 mg of Fe/kg per day [Semin. Hematol., Vol. 27, Brittenham, "Pyridoxal Isonicotinoyl Hydrazone: An Effective Iron-Chelator After Oral Administration," pages 112-116 (1990)].

Although considerable effort has been invested in the development of new therapeutics for managing thalassemia, the subcutaneous (sc) infusion of desferrioxamine B, a hexacoordinate hydroxamate iron chelator produced by Streptomyces pilosus [Helv. Chim. Acta, Vol. 43, Bickel et al, "Metabolic Properties of Actinomycetes. Ferrioxamine B," pages 2129-2138 (1960)], is still the protocol of choice. Although the drug's efficacy and long-term tolerability are well-documented, it suffers from a number of shortcomings associated with low efficiency and marginal oral activity.

Although a substantial number of synthetic iron chelators have been studied in recent years as potential orally active therapeutics, e.g., pyridoxyl isonicotinoyl hydrazone (PIH) [FEBS Lett., Vol. 97, Ponka et al, "Mobilization of Iron from Reticulocytes: Identification of Pyridoxal Isonicotinoyl Hydrazone as a New Iron Chelating Agent," pages 317-321 (1979)], hydroxypyridones [J. Med. Chem., Vol. 36, Uhlir et. al, "Specific Sequestering Agents for the Actinides. 21. Synthesis and Initial Biological Testing of Octadentate Mixed Catecholate-hydroxypyridinonate Ligands," pages 504-509 (1993); and Lancet, Vol. 1, Kontoghiorghes et al, "1,2 -Dimethyl-3-hydroxypyrid-4-one, an Orally Active Chelator for the Treatment of Iron Overload," pages 1294-1295 (1987)] and bis(o-hydroxybenzyl)-ethylenediaminediacetic acid (HBED) analogues [Ann. N.Y. Acad. Sci., Vol. 612, Grady et al, "HBED: A Potential Oral Iron Chelator," pages 361-368 (1990)), none has yet proven to be completely satisfactory. Interestingly, the siderophores have remained relatively untouched in this search. Their evaluation as iron-clearing agents has not at all paralleled the rate of their isolation and structural elucidation. In fact, until recently, beyond DFO, only two of some 100 siderophores identified have been studied in animal models: enterobactin [Gen. Pharmac., Vol. 9, Guterman et al, "Feasibility of Enterochelin as an Iron-Chelating Drug: Studies with Human Serum and a Mouse Model System," pages 123-127 (1978)] and rhodotorulic acid [J. Pharmacol. Exp. Ther., Vol. 209, Grady et al, "Rhodotorulic Acid-Investigation of its Potential as an Iron-Chelating Drug," pages 342-348 (1979)]. While the former was only marginally effective at clearing iron, the latter compound was reasonably active. Unfortunately, both of these cyclic siderophores exhibited unacceptable toxicity, and neither possessed any oral activity. They were abandoned as there were any number of synthetic chelators with equally unsatisfactory properties from which to choose.

U.S. patent application Ser. No. 08/624,289 filed Mar. 29, 1996, the entire contents and disclosure of which are incorporated herein by reference, discloses certain 2-pyridyl-$\Delta^2$-thiazoline-4-carboxylic acids and derivatives thereof useful for the treatment of human and non-human animals in need of therapy entailing the prevention of deposition of trivalent metals and compounds thereof in their tissues, as well as the elimination of such metals and compounds from biological systems overloaded therewith.

It is an object of the present invention to provide additional novel thiazoline acids and derivatives thereof which, because of different volumes of distribution in patients and different lipophilicities than the derivatives of the prior art, provide the ability to control the pharmacokinetic properties and toxicities of the drugs.

Another object of the present invention is to provide novel pharmaceutical compositions for and methods of treatment of human and non-human animals in need of therapy entailing the prevention of deposition of trivalent metals and compounds thereof in tissues thereof, as well as the elimination of such metals and compounds from systems overloaded therewith.

SUMMARY OF THE INVENTION

The above and other objects are realized by the present invention, one embodiment of which comprises compounds of the formula:

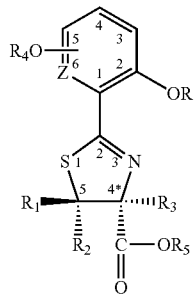

wherein: Z is CH or N;

R is H or acyl;

$R_1$, $R_2$, $R_3$ and $R_5$ may be the same or different and represent H, alkyl or hydrocarbyl arylalkyl having up to 14 carbon atoms; and $R_4$ is H or alkyl having 1-4 carbon atoms;

a salt thereof with a pharmaceutically acceptable acid or a pharmaceutically acceptable complex thereof.

Another embodiment of the invention relates to pharmaceutical compositions in unit dosage form comprising a therapeutically effective amount of the above compound and a pharmaceutically acceptable carrier therefor.

An additional embodiment of the invention concerns methods of preventing or treating a pathological condition in a human or non-human animal that is associated with an excess of a trivalent-metal, ion or compound thereof comprising administering to the animal a therapeutically effective amount of the compound defined above.

BRIEF DESCRIPTION OF THE DRAWING

The Figure depicts a reaction scheme for preparing the compounds of the invention.

DETAILED DESCRIPTION OF THE INVENTION

The present invention is predicated on the discovery that compounds of the above formula are valuable bioactive chelators or sequestrants for trivalent metals such as Fe, Al and Cr. They can be administered to human and non-human mammals to prevent the deposition of, e.g., iron, in the tissues thereof. They are also useful for the elimination of, e.g., iron, from such mammals afflicted with, e.g., haemochromatosis, haemosiderosis and also cirrhosis. They also find application in dialysis, encephalopathy, osteomalacia and Alzheimer's disease.

The compounds described above are characterized by the asymmetric carbon atom marked with an asterisk (*). The bonds surrounding these carbon atoms are arranged tetrahedrally and the substituents thus bonded to the asymmetric carbon atoms are in fixed positions. The formula represents optical antipodes exhibiting either the (S) or (R) conformation as shown in (i) and (ii) below:

(S) conformation

(R) conformation

In the above formula, R is preferably H, but may also be a suitable acyl group which is cleavable under physiological conditions to the free hydroxyl compounds and a biologically acceptable acid. Such acyl groups are known in the art, e.g., the acyl radical of a carbonic acid semiester, in particular carbonic acid semi-$C_1$-$C_4$-alkyl ester or carbonic acid semi-oxaalkyl ester in which oxaalkyl has 4-13 chain members such as an acyl radical —C(=O)—(O—$CH_2$—$CH_2$)$_n$—O-Alk in which n is an integer from 0 to 4 and Alk represents $C_1$-$C_4$ alkyl, in particular methyl or ethyl. Such acyl groups are, for example, methoxycarbonyl, ethoxycarbonyl or 2-(methoxyethoxy)-ethoxycarbonyl. Further acyl radicals are, for example, $C_1$-$C_3$-alkanoyl such as acetyl or propionyl, or mono-substituted or di-substituted carbamoyl such as di-$C_1$-$C_4$-alkyl carbamoyl, for example, dimethylcarbamoyl or diethylcarbamoyl, or $C_1$-$C_4$-alkoxycarbonyl-$C_1$-$C_4$-alkyl-carbamoyl, for example, methoxycarbonyl, ethylcarbamoyl, ethoxycarbonylmethylcarbamoyl or 2-ethoxycarbonylethyl-carbamoyl.

$R_1$, $R_2$, $R_3$ and $R_5$ may be the same or different and may be H, straight or branched chain alkyl having up to 14 carbon atoms, e.g., methyl, ethyl, propyl and butyl or arylalkyl wherein the aryl portion is hydrocarbyl and the alkyl portion is straight or branched chain, the arylalkyl group having up to 14 carbon atoms.

$R_4$ is H or straight or branched chain alkyl having 1 to 4 carbon atoms, e.g., methyl, ethyl, n-propyl, isopropyl, n-butyl, isobutyl, t-butyl.

Preferred among compounds of the above formula are those of the formula:

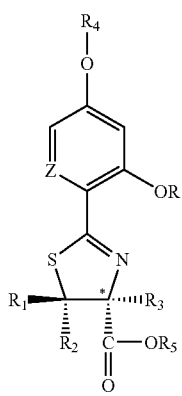

wherein: Z, R, $R_1$, $R_2$, $R_3$, $R_4$ and $R_5$ have the meanings ascribed above, as well as salts thereof with pharmaceutically acceptable acids and pharmaceutically acceptable complexes thereof.

Particularly preferred are those compounds of the above formula wherein:
a. Z is CH and R=$R_1$=$R_2$=$R_3$=$R_4$=$R_5$=H;
b. Z is N and R=$R_1$=$R_2$=$R_3$=$R_4$=$R_5$=H;
and most preferably, the optically pure isomers thereof.

It will be understood that salts of the compounds of the above formula with pharmaceutically acceptable acids also comprise part of the present invention. Suitable such acids include hydrochloric, sulfuric or phosphoric acids, as well as methanesulfonic, arginine, lysine, and the like.

The invention also includes pharmaceutically acceptable salts of the carboxylic acids of the above formula. Thus, ammonium salts and metal salts such as the alkali metal and alkaline earth metals salts, e.g., sodium, potassium, magnesium or calcium salts, as well as divalent metal salts such as zinc, and salts with suitable organic amines, there coming into consideration such salt formation especially aliphatic, cycloaliphatic, cycloaliphatic-aliphatic or araliphatic primary, secondary or tertiary mono-, di- or poly-amines, and also heterocyclic bases. Such amines are, for example, lower alkylamines, for example, triethylamine, hydroxy-lower alkylamines, for example, 2-hydroxyethylamine, bis-(2-hydroxy-ethyl)-amine or tris-(2-hydroxyethyl)-amine, basic aliphatic esters of carboxylic acids, for example, 4-aminobenzoic acid 2-diethylaminoethyl ester, lower alkyleneamines, for example, 1-ethylpiperidine, cycloalkylamines, for example, dicyclohexylamine, or benzylamines, for example, N,N'-dibenzyl-ethylenediamine, also bases of the pyridine type, for example, pyridine, collidine or quinoline. Further salts include internal salts (zwitterionic forms of compounds of the invention), wherein a basic group, for example, the basic nitrogen atom present in the pyridine ring, is protonated by a hydrogen ion originating from an acid group in the molecule.

Owing to their high solubility and good tolerability, metal ion complexes of compounds of the above formulae, especially with suitable paramagnetic and/or radioactive metals, can be used as contrast agents in diagnostic medicine, for example, X-ray, radionuclide, ultrasound and/or magnetic resonance diagnostics.

Compounds of the above formulae may be synthesized according to the reaction scheme set forth in The Figure wherein D-cys is D-cysteine or a reactive functional derivative thereof.

Free hydroxy groups present in the compounds of the above formulae are optionally protected by conventional protecting groups. Such protecting groups protect the hydroxy groups from undesired condensation reactions, substitution reactions and the like. The protecting groups can be introduced and removed easily, i.e., without undesirable secondary reactions taking place, for example, by solvolysis or reduction, in a manner known per se. Protecting groups and the methods by which they are introduced and split off are described, for example, in "Protective Groups in Organic Chemistry," Plenum Press, London, N.Y. (1973) and also in "Methoden der organischen Chemie," Houben-Weyl, 4th edition, Vol. 15/1, Georg Thieme Verlag, Stuttgart (1974).

Suitable hydroxy-protecting groups are, for example, acyl radicals such as lower alkanoyl optionally substituted, for example, by halogen such as 2,2-dichloroacetyl, or acyl radicals of carbonic acid semiesters, especially tert.-butoxycarbonyl, optionally substituted benzyloxycarbonyl, for example, 4-nitrobenzyloxycarbonyl, or diphenylmethoxycarbonyl, alkenyloxycarbonyl, for example, allyloxycarbonyl, or 2-halo-lower alkoxycarbonyl such as 2,2,2-trichloroethoxycarbonyl, also trityl or formyl, or organic silyl radicals, also etherifying groups that can readily be split off such as tert.-lower alkyl, for example, tert.-butyl, or 2-oxa- or 2-thiacycloalkyl having 5 or 6 ring atoms, for example, tetra-hydrofuryl or 2-tetrahydropyranyl or corresponding thia analogues, and also optionally substituted 1-phenyl-lower alkyl such as optionally substituted benzyl or diphenylmethyl, there coming into consideration as substituents of the phenyl radicals, for example, halogen such as chlorine, lower alkoxy such as methoxy, and/or nitro.

A reactive functional derivative of a carboxy group (Y) is, for example, an acid anhydride, an activated ester or an activated amide, cyano, a group of the formula —C(OR$_a$)$_3$ or —C(=NH)—R$_a$ in which R$_a$ is lower alkyl. Corresponding derivatives are well known in the art.

Of the anhydrides, the mixed anhydrides are especially suitable. Mixed anhydrides are, for example, those with inorganic acids such as hydrohalic acids, i.e., the corresponding acid halides, for example, chlorides or bromides, also with hydrazoic acid, i.e., the corresponding acid azides. Further mixed anhydrides are, for example, those with organic carboxylic acids such as with lower alkanecarboxylic acids optionally substituted, for example, by halogen such as fluorine or chlorine, for example, pivalic acid or trichloroacetic acid, or with semiesters, especially lower alkyl semiesters of carbonic acid such as the ethyl or isobutyl semiester of carbonic acid, or with organic, especially aliphatic or aromatic, sulfonic acids, for example, p-toluenesulfonic acid. Of the activated esters, there may be mentioned, for example, esters with vinylogous alcohols (i.e., enols such as vinylogous lower alkenols), or iminomethyl ester halides such as dimethyliminomethyl ester chloride (prepared from the carboxylic acid and, for example, dimethyl-(1-chlorethylidine)-iminium chloride of the formula $(CH_3)_2N^{\oplus}=C(Cl)CH_3Cl^{\ominus}$, which can be obtained, for example, from N,N-dimethylacetamide and phosgene), or aryl esters such as preferably suitable substituted phenyl esters, for example, phenyl ester substituted by halogen such as chlorine; and/or by nitro, for example, 4-nitrophenyl ester, 2,3-dinitrophenyl ester or 2,3,4,5,6-pentachlorophenyl ester, N-hetero-aromatic esters such as N-benztriazole esters, for example, 1-benztriazole ester, or N-diacylimino esters such as N-succinylamino or N-phthalylimino ester. Suitable activated amides are, for example, imidazolides, also 1,2,4-triazolides, tetrazolides or 1,2,4-oxadiazolinonides.

A preferred form of this process according to the invention is the reaction of a compound of the nitrile with a cysteine derivative. The reaction is carried out in an inert solvent such as an aqueous solvent at ambient temperature or, preferably, at slightly elevated temperature, for example, at about 50° to 80° C., and preferably under an inert gas atmosphere.

In resulting compounds in which one or more functional (hydroxy) groups are protected, the latter can be freed, optionally in stages or simultaneously, in a manner known per se, by means of solvolysis, especially hydrolysis or acidolysis, or in some cases also by means of careful reduction. Silyl protecting groups are advantageously split off with fluorides, for example, tetraethylammonium fluoride.

Salts of compounds of the invention can be manufactured in a manner known per se. Thus, salts of compounds having acidic groups can be formed, for example, by treating with metal compounds such as alkali metal salts of suitable organic carboxylic acids, for example, the sodium salt of α-ethylcaproic acid, or with inorganic alkali metal or alkaline earth metal salts, for example, sodium bicarbonate, or with ammonia or a suitable organic amine, preferably stoichiometric quantities or only a small excess of the salt-forming agent being used. Acid addition salts of compounds of the invention are obtained in a customary manner, for example, by treating with an acid or a suitable anion-exchange reagent. Internal salts of compounds of the invention (zwitterionic forms) can be formed, for example, by neutralizing the compounds or salts such as acid addition salts, to the isoelectric point, for example, with weak bases, or by treating with liquid ion exchangers.

Salts can be converted in a customary manner into the free compounds: metal and ammonium salts can be converted into the free compounds, for example, by treating with suitable acids, and acid addition salts, for example, by treating with a suitable basic agent.

The starting materials are available commercially and/or known or can be manufactured by known processes.

The racemate can be split in a manner known per se, for example, after conversion of the optical antipodes into diastereoisomers, for example, by reaction with optically active acids or bases.

The pharmacologically acceptable compounds of the present invention can be used, for example, for the manufacture of pharmaceutical compositions which contain an effective amount of the active substance together or in admixture with inorganic or organic, solid or liquid, pharmaceutically acceptable carriers.

The pharmaceutical compositions according to the invention are those which are suitable for enteral, such as oral, administration and for parenteral, such as subcutaneous, administration to warm blooded animals, especially humans, and which contain the pharmacologically active substance on its own or together with a pharmaceutically acceptable carrier. The dosage of the active substance depends on the species of warm-blooded animal and on the age and individual condition, the illness to be treated and also on the mode of administration.

The novel pharmaceutical preparations contain from approximately 10% to approximately 95%, and preferably from approximately 20% to approximately 90%, of the active substance. Pharmaceutical compositions according to the invention can, for example, be in unit dose form, such as dragées, tablets, capsules, suppositories or ampoules, and contain from approximately 0.05 g to approximately 10.0 g, and preferably from approximately 0.3 g to approximately 1.0 g, of the active ingredient.

The pharmaceutical compositions of the present invention are manufactured in a manner known per se, for example, by means of conventional mixing, granulating, confectioning, dissolving or lyophilizing processes. Pharmaceutical compositions for oral use can be obtained by combining the active substance with one or more solid carriers, if desired, granulating a resulting mixture and processing the mixture or granulate, if desired or necessary after the addition of suitable adjuncts, to form tablets or dragée cores. In so doing, they can also be incorporated into plastics carriers which release the active substances or allow them to diffuse in controlled amounts.

Suitable carriers are especially fillers such as guars, for example, lactose, saccharose, mannitol or sorbitol, cellulose preparations and/or calcium phosphates, for example, tricalcium phosphate or calcium hydrogen phosphate, also binders such as starches, for example, corn, wheat, rice or potato starch, gelatine, tragacanth, methylcellulose, hydroxypropylmethylcellulose, sodium carboxymethylcellulose and/or polyvinylpyrrolidone, and/or; if desired, disintegrators such as the above-mentioned starches, also carboxymethyl starch, cross-linked poly-vinyl pyrrolidone, agar, alginic acid or a salt thereof such as sodium alginate. Adjuncts are especially flow-regulating and lubricating agents, for example, silica, talc, stearic acid or salts thereof such as magnesium or calcium stearate, and/or polyethylene glycol. Dragée cores are provided with suitable coatings that are, if desired, resistant to gastric juice, there being used, inter alia, concentrated sugar solutions which optionally contain gum arabic, talc, polyvinylpyrrolidone, polyethylene glycol and/or titanium dioxide, lacquer solutions in suitable organic solvents or solvent mixtures or, for the manufacture of coatings that are resistant to gastric juice, solutions of suitable cellulose preparations such as acetyl-cellulose phthalate or hydroxypropylmethylcellulose phthalate. Coloring substances or pigments can be added to the tablets or dragée coatings, for example, for the purpose of identification or for indicating different doses of active substance.

Other orally administrable pharmaceutical compositions are dry-filled capsules made of gelatin and also soft, sealed capsules made of gelatin and a plasticizer such as glycerol or sorbitol. The dry-filled capsules may contain the active ingredient in the form of a granulate for example, in admixture with fillers such as corn starch, binders and/or glidants such as talc or magnesium stearate and optionally stabilizers in soft capsules, the active ingredient is preferably dissolved or suspended in suitable liquids or wax-like substances such as fatty oils, paraffin oil or polyethylene glycols, it being possible also for stabilizers to be added.

Other forms of oral administration are, for example, syrups prepared in a customary manner that contain the active ingredient in, for example, suspended form and in a concentration of approximately from 5% to 20%, and preferably approximately 10%, or in a similar concentration that provides a suitable single dose when administered, for example, in measures of 5 or 10 ml. Also suitable are, for example, powdered or liquid concentrates for preparing shakes, for example, in milk. Such concentrates can also be packed in single-dose quantities.

Particularly suitable dosage forms for parenteral administration are sterile aqueous solutions of an active ingredient in water-soluble form, for example, a water-soluble salt, or sterile aqueous injection suspensions which contain substances increasing the viscosity, for example, sodium, carboxymethyl cellulose, sorbitol and/or dextran, and optionally stabilizers. In addition, the active ingredient, with or without adjuvants, can also be in lyophilized form and brought into solution prior to parenteral administration by the addition of suitable solvents.

The invention also relates to compositions for diagnostic purposes that contain a suitable metal complex of a compound of the formula wherein Z, R, $R_1$, $R_3$, $R_4$ and $R_5$ are as previously defined.

The invention also relates to a method of treatment of pathological conditions in a mammal, especially human, which as has been described hereinabove, are associated with an excess of a trivalent metal cation such as aluminum or, especially, iron (III), in the body, which method comprises administering, preferably orally, a prophylactically or therapeutically effective amount of a compound of the formula or of a pharmaceutically acceptable salt thereof. There are used for this purpose especially the above-mentioned pharmaceutical compositions, a daily dose of from approximately 50 mg to approximately 10,000 mg, and preferably from approximately 300 mg to approximately 1,000 mg, of a compound of the present invention being administered to a warm-blooded animal of approximately 70 kg body weight. The dosage can be administered orally in several, for example, three, individual doses. For systemic, e.g., subcutaneous, administration, the more water-soluble salt forms of the compounds of the formula, e.g., the sodium salt, are preferred, for example, orally, or alternatively, subcutaneously.

The following examples serve to illustrate the invention, but should not be construed as a limitation thereof. Temperatures are given in degrees Centigrade.

Preparation of Drugs. Drug solutions were prepared in 60% water, 40% Cremophor RH-40.

EXAMPLE 1

2,4-Dihydroxybenzonitrile was prepared according to the method of Marcus in *Ber. dtsch. chem. Ges.* 1981, 24, 3651, as follows:

A mixture of 2,4-dihydroxybenzaldehyde (5.0 g, 36.2 mmol), sodium acetate (5.94 g, 72:4 mmol), nitroethane (5.44 g, 72.4 mmol) and glacial acetic acid (10 ml) was refluxed for 6 hours. After cooling, the mixture was poured onto ice (100 g) and extracted with ethyl acetate (4×50 ml). The combined organic layers were washed with saturated $NaHCO_3$ until the pH of the aqueous layer remained at 8, dried ($Na_2SO_4$) and the solvent removed in vacuo. Flash chromatography ($SiO_2$, cyclohexane:ethyl acetate=1:1) afforded 2,4-dihydroxybenzonitrile (2.87 g, 59%) as a pale yellow solid. $^1H$ NMR (300 MHz, DMSO-$d_6$) δ 6.33 (d, 1H, J=8.6 Hz), 6.43 (s, 1H), 7.37 (d, 1H, J=8.6 Hz), 10.35 (s, 1H), 10.78 (s, 1H). IR (KBr) 2200 $cm^{-1}$.

EXAMPLE 2

4,5-Dihydro-2-(2,4-dihydroxyphenyl)-thiazole-4(S)-carboxylic acid was prepared as follows:

D-cysteine hydrochloride monohydrate (6.8 g, 38.7 mmol) was added to a solution of 2,4-dihydroxybenzonitrile (3.5 g, 25.9 mmol) prepared in Example 1, in a mixture of degassed methanol (1.05 ml) and 0.1 M phosphate buffer, pH 5.95 (70 ml). $NaHCO_3$ (3.25 g, 38.7 mmol) was carefully added and the mixture was stirred at 70° C. under Ar for 54 hours. Volatile components were removed under reduced pressure and the solution was acidified with 1 N HCl to pH 2. The resulting brown precipitate was vacuum filtered and the solid was washed with water (40 ml) and ethanol (20 ml). The crude product was dissolved in saturated $NaHCO_3$ (700 ml) and the aqueous solution washed with ethyl acetate (2×200 ml). The aqueous layer was filtered through a fine frit and acidified with 1 N HCl to pH 2. The precipitated product was vacuum filtered. The aqueous layer was extracted with ethyl acetate (4×400 ml), the combined organic extracts were dried ($Na_2SO_4$) and the solvent was removed in vacuo. The remaining solid was combined with the precipitated product and dried under high vacuum at 40° C. for 12 hours to give 4,5-dihydro-2-(2,4-dihydroxyphenyl)-thiazole-4(S)-carboxylic acid (4.08 g, 66%), mp 266-268° C. (dec) [*Ind. J. Chem.*, Vol. 15B, Kishore et al, pages 255-257 (1977) for (L)-isomer: 261-262° C.]. $^1H$ NMR (300 MHz, DMSO-$d_6$) δ 3.61 (m, 2H), 5.38 (dd, 1H, J=7.2/9.4 Hz), 6.31 (d, 1H, J=2.3 Hz), 6.38 (dd, 1H, J=2.3/8.6 Hz), 7.25 (d, 1H, J=8.6 Hz), 10.25 (br s, 1H), 12.60 (br s, 1H), 13.15 (br s, 1H). Anal. calc. for $C_{10}H_9NO_4S$: C 50.20, H 3.79, N 5.85. Found: C 50.13, H 3.82, N 5.85.

Compounds of the invention in the scheme of FIG. 1 wherein Z is N may be prepared as described above in Examples 1 and 2 substituting the corresponding pyridyl aldehyde for 2,4-dihydroxybenzaldehyde.

The biological activity and properties of the compounds of the invention were evaluated as follows employing 4,5-dihydro-2-(2,4-dihydroxyphenyl)-thiazole-4(S)-carboxylic acid (1).

EXAMPLE 3

In Rats

Initial testing of 1 was performed in the non-iron-overloaded, bile duct-cannulated rat [*J. Med. Chem.*, Vol. 34, Bergeron et al, "Synthesis and Biological Evaluation of Hydroxamate-Based Iron Chelators," pages 3182-3187 (1991)]. The drug was prepared as a solution in 40% Cremophor-$H_2O$ and administered at a dose of 150 µmol/kg p.o. The rats were fasted for 24 hours before dosing. The efficiency of iron excretion induced by 1 was 2.4±0.92%.

EXAMPLE 4

In Monkeys

Given the results in the rat model, the ability of 1 to promote iron excretion in the iron-overloaded primate model [*Blood*, Vol. 79, Bergeron et al, "A Comparison of the Iron-Clearing Properties of 1,2-Dimethyl-3-Hydroxypyrid-4-One, 1,2-Diethyl-3-Hydroxypyrid-4-One and Deferoxamine," pages 1882-1890 (1992)] was evaluated. The drug was prepared as a solution in 40% Cremophor-$H_2O$ and administered at a dose of 1.50 µmol/kg p.o. The monkeys were fasted for 24 hours before dosing. Immediately prior to drug administration, the monkeys were sedated with ketamine (7-10 mg/kg. i.m.) and given scopolamine (0.04-0.07 mg/kg/i.m. to prevent ketamine-related salivation and vomiting. At the dose of 150 µmol/kg, the efficiency of 1 was 4.2±1.4% (n=4).

What is claimed is:

1. A method of preparing a compound of the formula:

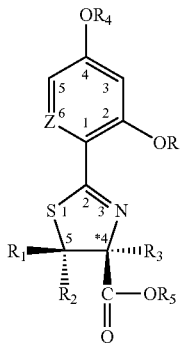

wherein:

Z is CH or N;

R is H or acyl;

$R_1$, $R_2$, $R_3$ and $R_5$ may be the same or different and represent H, alkyl or hydrocarbyl arylalkyl having up to 14 carbon atoms;

$R_4$ is H or alkyl having 1-4 carbon atoms, and salts thereof with a pharmaceutically acceptable acid, comprising reacting a first reagent of the formula:

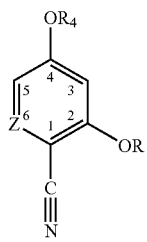

with a second reagent of the formula:

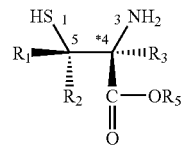

or a salt thereof with a pharmaceutically acceptable acid.

2. The method of claim 1, wherein the first and second reagents are reacted in an inert solvent or a mixture of inert solvents.

3. The method of claim 2, wherein the inert solvent or the mixture is aqueous.

4. The method of claim 2, wherein the mixture comprises an aqueous solvent and an alcohol.

5. The method of claim 4, wherein the aqueous solvent is a phosphate buffer.

6. The method of claim 4, wherein the alcohol is methanol.

7. The method of claim 4, wherein the mixture comprises a phosphate buffer and methanol.

8. The method of claim 2, wherein the first and second reagents are reacted at ambient temperature.

9. The method of claim 2, wherein the first and second reagents are reacted at a temperature from about ambient temperature to about 80° C.

10. The method of claim 9, wherein the temperature is from about 50° C. to about 80° C.

11. The method of claim 10, wherein the temperature is about 70° C.

12. The method of claim 2, wherein the first and second reagents are reacted under an inert gas atmosphere.

13. The method of claim 1, wherein the first and second reagents are reacted in the presence of a base.

14. The method of claim 13, wherein the base is $NaHCO_3$.

15. The method of claim 1, wherein Z is CH.

16. The method of claim 15, wherein $R=R_1=R_2=R_4=R_5=H$.

17. The method of claim 1, wherein Z is N.

18. The method of claim 1, wherein Z is CH and $R_3$ is an alkyl having 1-4 carbon atoms.

* * * * *